United States Patent [19]

Cockerill

[11] 4,183,947

[45] Jan. 15, 1980

[54] NUTRITIONAL AND THERAPEUTIC IRON COMPOSITION AND METHOD OF MAKING

[76] Inventor: Vernon L. Cockerill, 1000 Macomb Rd., Rushville, Ill. 62681

[21] Appl. No.: 847,741

[22] Filed: Nov. 2, 1977

Related U.S. Application Data

[63] Continuation-in-part of Ser. No. 759,004, Jan. 13, 1977, abandoned.

[51] Int. Cl.$^2$ .............................................. A61K 31/295
[52] U.S. Cl. .................................. 424/295; 260/439 R
[58] Field of Search ...................... 424/295; 260/439 R

[56] References Cited

U.S. PATENT DOCUMENTS

| | | | |
|---|---|---|---|
| 2,877,253 | 3/1959 | Rummel | 260/439 |
| 2,957,806 | 10/1960 | Rummel | 424/295 |
| 2,957,806 | 10/1960 | Rummel | 424/147 |
| 3,168,541 | 2/1965 | Hobbs | 260/439 |

OTHER PUBLICATIONS

Chattem Chemicals Bulletin No. TDG-12, Chattanooga, Tenn. 37409.
Svajgr–Feedstuffs, Mar. 8, 1976.
Brady et al.–J. Animal Science, vol. 41 (1975), p. 255.
Rummel et al.–Chem. Abst., vol. 51, (1957), p. 6879f.
Bukanova et al.–Chem. Abst., vol. 69, (1968), p. 83040m.
Rummel–Chem. Abst., vol. 55 (1961), p. 8775h.
Eiichi et al.–Chem. Abst., vol. 61, (1964), p. 4162a.

*Primary Examiner*—Sam Rosen
*Attorney, Agent, or Firm*—Merriam, Marshall & Bicknell

[57] ABSTRACT

A nutritional and therapeutic source of iron comprising an orally administrable composition having as the essential source of iron the reaction product of one molar equivalent of a ferrous iron salt and at least two molar equivalents of glycine and said ferrous iron in said reaction product being in a non-ionic form with each ferrous iron molecule having two glycine molecules ionically bonded therewith and preferably also having six molecules of glycine associated therewith by covalent bonds and said reaction product when orally administered in a liquid or solid feed mixture or in an aqueous solution to mammals effecting a significant increase in the concentration of iron in the blood of the mammals.

12 Claims, No Drawings

NUTRITIONAL AND THERAPEUTIC IRON COMPOSITION AND METHOD OF MAKING

This application is a continuation-in-part application of Serial No. 759,004, filed January 13, 1977, now abandoned.

The present invention relates generally to an improved iron composition which provides a nutritional source of iron and is physiologically useful for the prevention and treatment of iron deficiency anemia in mammals when used alone or as an adjunct in the treatment of other types of anemia.

It has long been recognized that iron is an essential component in the blood of mammals and must be present in at least certain minimal amounts in order to maintain normal body growth and functions. It is particularly essential for the production of hemoglobin, a deficiency of which is said to be anemia. When hemoglobin deficiency is caused by insufficient iron in the blood, it is called iron deficiency anemia. Although hemoglobin deficiency may be caused by other factors, such as lack of vitamins and protein, iron should also be administered when treating one of the latter deficiencies in order to provide adequate treatment of the hemoglobin deficiency.

Anemia is one of the most common nutritional and medical problems of both man and animals in the world today, especially in young, growing or pregnant mammals, and when the mammal is bred back soon after delivery, and during the menstrual cycle when increased volumes of blood are being produced. It is also a major problem of mammals consuming iron deficient foods or foods in which the iron is bound in an unabsorbable form.

It is general knowledge that iron must be in the ferrous form ($Fe^{++}$) as opposed to the ferric form ($Fe^{+++}$) in order to be absorbed in significant amounts from the intestinal tract. However, most iron in food when ingested is in the ferric form and is reduced to ferrous iron in the digestive tract to a very limited degree (i.e. only about 5-10% of the iron ingested). The ferrous iron reacts with hydrochloric acid in the stomach to form ferrous chloride which in turn reacts with certain compositions in the stomach to form compounds which can be absorbed from the intestinal tract. The ferrous ion ($Fe^{++}$) unfortunately can also react with many other compounds in the stomach and gastrointestinal tract to form iron products which cannot be absorbed from the intestinal tract, thereby decreasing the amount of ingested iron absorbed.

Among the ferrous iron salts which have been proposed for treating iron deficiency anemia is the ferrous sulfate-glycine reaction product (ferroglycine sulfate) formed by reacting ferrous sulfate and glycine in equal molar amounts to provide a compound which can be represented by the following structural formula:

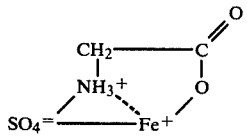

The foregoing ferroglycine sulfate product has been disclosed in U.S. Pat. No. 2,957,806 as being well absorbed from the intestinal tract of fasting mammals. However, this ferrous sulfate-glycine product is unstable in normal tap water and is also unstable under the conditions normally encountered in the intestinal tract of mammals being fed a normal diet, particularly suckling mammals, Thus, it has been found that ferroglycine sulfate formed by reacting equimolar amounts of ferrous iron and glycine is unstable in the intestinal tract of mammals being fed a normal diet and, therefore, is entirely unsatisfactory for providing a supplemental nutritional source of iron by oral administration in drinking water or as a supplement in a food mixture. Studies show that there is no advantage in favor of the ferroglycine sulfate product in either tolerance or efficacy over ferrous sulfate when these compounds are orally administered (see *New England Journal of Medicine*, Vol. 267—No. 11, page 538, 1962, "Relative Effectiveness of Ferroglycine Sulfate and Ferrous Sulfate").

It is an object of the present invention to provide a process of producing a nutritionally useful form of iron which has improved stability and absorption efficiency.

It is a further object of the present invention to provide a process of producing a pharmacologically active form of iron useful for the treatment of iron deficiency anemia.

It is also an object of the present invention to provide a process for producing an improved reaction product of ferrous iron and glycine useful as a nutritional source of iron.

It is another object of the present invention to provide an improved method of raising the iron content of the blood of mammals, and particularly for mammals such as sows and suckling piglets.

It is still another object of the present invention to provide an improved method of supplying mammals, particularly suckling piglets and sows, with a pharmacologically useful form of iron for the prevention and treatment of iron deficiency anemia.

It is a further object of the present invention to provide an improved orally administerable form of iron which is nutritionally and physiologically effective for increasing the hemoglobin levels in the blood of mammals, particularly suckling mammals, such as piglets and sows.

It is still another object of the present invention to provide a nutritionally and physiologically useful form of ferrous iron and glycine which is stable in the pH range encountered in the intestinal tract of a normally fed mammal, including suckling pigs and sows.

It is a further object of the present invention to provide a nutritionally and pharmacologically useful form of ferrous iron and glycine which is stabilized against rapid degradation in the gastric intestinal tract of normally fed mammals.

It is also an object of the present invention to provide a nutritionally and pharmacologically useful reaction product of ferrous chloride and glycine which when fed orally to mammals deficient in iron raises the hemoglobin concentration in the blood to a level much higher than previously attainable by other orally administered forms of iron.

It is another object of the present invention to provide a process of forming an improved orally administerable ferrous glycine composition as a nutritional source of iron.

It is still another object of the present invention to provide a process of forming an improved ingestible reaction product of ferrous iron and glycine useful as a nutritional source of iron.

Other objects of the invention will be apparent to those skilled in the art from the following detailed description and accompanying claims.

It has been discovered that an improved nutritional source of iron which is readily assimilated and which has a high degree of stability under the conditions encountered in the intestinal tract of mammals being fed a normal diet, including suckling mammals, and in dry mixtures with solid edible feed material, and in tap water within a pH range of between about pH 1 and about pH 4.5 can be prepared by reacting in an aqueous solution one molar equivalent of a non-toxic ferrous iron compound, such as ferrous chloride or ferrous sulfate, with at least two molar equivalents of glycine so as to form the compound ferrous iron 2-glycine in which the two glycine molecules are ionically bound to the ferrous iron molecule and so that the ferrous iron is maintained in the non-ionic state.

The reaction and reaction product formed by reacting one molar equivalent of a ferrous salt and two molar equivalents of glycine is designated as a ferrous 2-glycine compound and can be represented by the following equation and structural formulae:

(A) $NH_2CH_2COOH \rightleftharpoons NH_3^+CH_2COO^-$ (glycine)

(B)
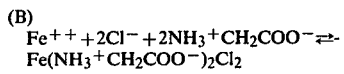
$Fe^{++} + 2Cl^- + 2NH_3^+CH_2COO^- \rightleftharpoons Fe(NH_3^+CH_2COO^-)_2Cl_2$

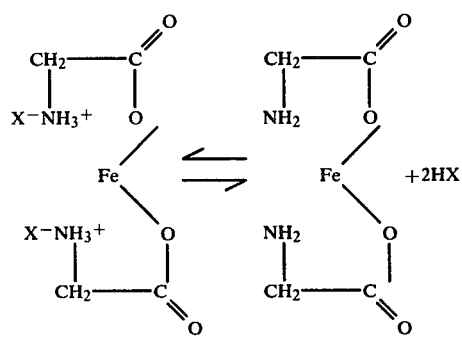

(C)

wherein "X" is a monovalent anion from a salt or acid, such as $FeCl_2$ or HCl.

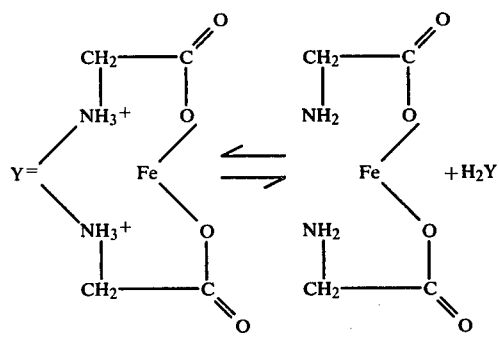

(D)

wherein "Y" is a divalent anion from salt or acid, such as $FeSO_4$ or $H_2SO_4$.

The ferrous 2-glycine reaction product can be complexed with up to six molecules of glycine and the latter reaction product can be represented by the following formula:

$(NH_2CH_2COOH)_6Fe(NH_3^+CH_2COO^-)_2X_n$ wherein "X" is monovalent or divalent anion, such as $Cl^-$ or $SO_4^=$, and n is 1 or 2. The latter reaction product is hereinafter designated a complex of ferrous 2-glycine and glycine or ferrous 8-glycine.

The ferrous 2-glycine reaction product is a distinct compound having the ferrous iron thereof in a non-ionic form rather than as an ionic iron compound, such as in ferroglycine sulfate heretofore proposed for the treatment of iron deficient anemia in U.S. Pat. No. 2,957,806. The improved stability and effectiveness of the reaction products of the present invention which provide a markedly improved nutritional source of iron and an improved method of treating iron deficiency anemia in mammals is thought to be the result of having the iron in the ferrous 2-glycine stabilized in the ferrous state with two molecules of glycine ionically bound to the ferrous iron. And, in the preferred ferrous 8-glycine the reaction product is further stabilized by having six additional molecules of glycine forming six covalent bonds with the ferrous iron molecule so that the reaction product is in the non-ionic form and also has a stable octet in the outer electron shell. In the latter form the ferrous iron is very stable and is capable of being almost quantitatively absorbed through the intestinal wall of the mammal and is neither precipitated as an insoluble iron compound nor readily transformed to the non-absorbable ferric state by reacting with oxygen or various components present in the gastro-intestinal tract of normally fed mammals.

It has been found that when a ferrous salt and glycine are reacted in a 1:2 molar ratio of iron to glycine and carbonate ions are added to an aqueous solution of the ferrous 2-glycine reaction product, some of the iron is precipitated. This can be largely overcome by adding excess glycine to the reaction solution so as to drive the reaction between the glycine and ferrous iron to completion. And, when each ferrous iron molecule has eight molecules of glycine associated therewith, two ionically bound and six bound by covalent bonds, the ferrous iron molecule is completely stabilized against reaction with water soluble carbonate irons. An excess of glycine binds any $Fe^{+++}$ ions present, thus preventing the $Fe^{+++}$ ions from displacing $Fe^{++}$ in the ferrous 2-glycine compound and preventing their conversion to $Fe^{+++}$ ions by oxidation. Adding excess glycine to a stabilized ferrous 8-glycine in an amount sufficient to combine with extraneous ions of other metals in the foods ingested, feed additives or in water further minimizes the problem of degradation of the ferrous 2-glycine compound or ferrous 8-glycine.

Acidifying an aqueous solution of the ferrous 2-glycine compound having up to six additional glycine molecules also improves the resistance of $Fe^{++}$ to oxidation and thereby improves their stability. In general, the lower the pH of the solution below pH 6.0, the more effective the stabilization. Since pH 4.0 to 4.5 is about the lowest pH that a substance can be reduced and remain very palatable, and since within this pH range $Fe^{++}$ resists oxidation to $Fe^{+++}$, the latter pH range is considered optimal for the stabilization of the ferrous 2-glycine compound and ferrous 8-glycine in an aqueous solution.

An edible organic acid, such as tartaric acid, succinic acid, ascorbic acid, citric acid or fumaric acid, is preferably used to effect lowering of the pH of the aqueous or solid carrier for the complex. And, since these organic acids are slowly absorbed acids, they maintain the pH of the gastrointestinal tract at a lower level longer than the more rapidly absorbed inorganic acids, such as hydrochloric acid. If desired, however, small amounts of a potable inorganic acid, such as hydrochloric acid which is also useful in preventing chloride ion deficiency anemia, can be used to partially or completely acidify the ferrous 2-glycine compound and the gastrointestinal tract. The ferrous 8-glycine can also be used simultaneously with pH buffers in amounts sufficient to lower the pH of the gastrointestinal tract of the mammal to pH 4.5 or below. Compounds that are both acidic that are both acidic and complexing agents for interfering metal ions tending to displace $Fe^{++}$ in the ferro 2-glycine, such as ascorbic acid, can be used to advantage. Citric acid stabilizes the ferric ion by forming soluble ferric citrate, thereby preventing the formation of ferric oxide. Fumaric acid has the advantage of being less hygroscopic than citric acid.

Another method of stabilizing the ferrous 2-glycine and glycine complex to prevent oxidation of $Fe^{++}$ to $Fe^{+++}$ is by using therewith substances that preferentially utilize the oxygen from the surrounding air or from the dissolved oxygen in solutions, such as sodium formaldehyde sulfoxalate, sodium bisulfite, butylated hydroxytoluene and butylated hydroxyanisole. Since the ferrous 2-glycine preparations contain no appreciable free $Fe^{++}$ ions, the foregoing antioxidant compounds of the present invention can be effectively used in the present invention, whereas they cannot be used for stabilizing ferrous 1-glycine. Butylhydroxy anisole and butyl hydroxy toluene are stable in the ferrous 2-glycine preparations and aid in the prevention of oxidation of $Fe^{++}$ to $Fe^{+++}$. And, while sodium formaldehyde sulfoxulate and sodium bisulfite are rapidly deactivated by acid conditions, when added in the small amount of about 0.5-1.0% to aqueous solutions of ferrous 2-glycine and are then tightly sealed in a container to prevent further contact with air, they effectively prolong the shelf life of the complex by preventing conversion of $Fe^{++}$ to $Fe_2O_3$.

Dry powder preparations can be further stabilized by coating the particles with water soluble or digestible preparations that prevent contact with air.

It should be understood that the ferrous 2-glycine compound having up to six covalent bonded molecules of glycine made in accordance with the present invention can be stabilized by any of the above described methods used singly or in combination.

The following specific examples are given in order to further illustrate the present invention without, however, limiting the invention to the particular materials or procedures used.

EXAMPLE I

One molar equivalent of ferrous chloride tetrahydrate (198.8 gms.) and slightly in excess of 2 molar equivalents of glycine (160 gms.) were dissolved in deionized water which was acidified to a pH of about 4.0 with hydrochloric acid. The reaction solution was preferably heated to a temperature of about 100° C. and preferably protected against contact with oxygen by placing the reaction vessel under a nitrogen atmosphere. A small amount of an antioxidant, such as butylhydroxyanisole, was preferably added to the reaction solution, particularly when the solution was not placed under a nitrogen atmosphere. The reaction proceeded rapidly to substantial completion forming ferrous 2-glycine hydrochloride. The ferrous iron of the compound was in the nonionic form and the reaction solution was essentially free of ferric ions. The ferrous 2-glycine can be recovered from the reaction solution as a precipitate by the addition of ethyl alcohol to the solution, or the aqueous solution per se can be administered in liquid form or can be further processed by spray drying to form a dry powder.

EXAMPLE II

A solution of ferrous chloride was prepared containing 1 gram mole of $FeCl_2$ (198.8 gms.) by dissolving ferrous chloride tetrahydrate salt in an aqueous 3% hydrochloric acid solution to form 334 mls. of a 38% aqueous acidic solution of ferrous chloride. Two (2) gram moles of glycine (150.15 gms.) were dissolved in the 334 mls. of 38% ferrous chloride solution while heating to boiling. The reaction solution was heated to a slow boil until the temperature of the reaction solution reached 152° C. The reaction solution was then poured into a teflon lined container and allowed to cool in a low humidity atmosphere until crystalized. The crystals formed were washed with dilute hydrochloric acid. The crystals formed assayed at 16% by wt. iron and corresponded to the tetrahydrate salt of ferrous 2-glycine hydrochloride having the formula: $Fe(NH_3+CH_2COO^-)_2Cl_2$. Heating the crystals at 120° C. yielded the anhydrous hydrochloride salt.

The tetrahydrate crystals had a glassy transparent brown appearance, were very soluble in water, had a sweetish non-astringent taste and were stable in dry air. The crystals formed a brown surface coating when stored in moist air. An aqueous solution of the ferrous 2-glycine hydrochloride salt was stable at a pH of 4.5 and below.

EXAMPLE III

Ferrous 2-glycine hydrosulfate was prepared by following the procedure of Example I using 278 grams of ferrous sulfate tetrahydrate in place of the ferrous chloride of Example I.

EXAMPLE IV

A solution of ferrous chloride was prepared containing 1 gram mole of ferrous chloride (198.8 gms.) by dissolving ferrous chloride tetrahydrate in an aqueous 3% hydrochloric acid solution to form 334 mls. of a 38% aqueous acidic solution of ferrous chloride. Eight (8) gram moles of glycine (600.6 gms.) were dissolved in the 334 mls. of 38% ferrous chloride solution while heating slowly to boiling. The reaction solution was heated at a slow boil until the temperature of the reaction solution reached 152° C. The reaction solution was then poured into a teflon lined container, and allowed to cool in a low humidity atmosphere until crystalized. The crystals were washed with 3% aqueous hydrochloric acid. The crystals were assayed at 6.99% iron and had a translucent tan appearance, was stable in dry air but formed a brown surface coating when stored in moist air, and had a sweet-sour lemonade-like taste. The crystals were very soluble in water and were stable in an aqueous solution at a pH of 4.5 or below.

EXAMPLE V

The ferrous 8-glycine hydrochloride product was prepared by dissolving 13.3 gms. of ferrous chloride tetrahydrate in 50 ml. of 3% aqueous hydrochloric acid. The ferrous chloride aqueous acidic solution having a pH of 4.0 was heated to boiling and 40 gms. of glycine dissolved therein. The reaction solution was slowly heated to remove water until the temperature of the solution reaches 152° C. The reaction mixture was poured onto a teflon sheet and allowed to cool to room temperature. The crystals formed on cooling were washed with dilute hydrochloric acid. The crystals had a light tan translucent appearance and when assayed were found to contain 96% of the iron in the ferrous state which was the same percent of iron in the ferrous form found in the original ferrous chloride tetrahydrate salt used in the reaction mixture. An aqueous solution of the ferrous 8-glycine did not form a precipitate when soluble carbonate ions were added to the solution.

EXAMPLE VI

To an aqueous acidic solution (pH 4.0) were added 198.8 grams of ferrous chloride (1 gram mole) and 600.6 gms. of glycine (8 gram mole equivalent) and allowed to react in solution. When aqueous sodium carbonate was added to a portion of the solution in an amount sufficient to react with all of the ferrous iron contained therein and filtered, all of the ferrous iron was found in the filtrate.

The remainder of the reaction solution was heated at a slow boil to effect removal of all water except the water of hydration (i.e. until the temperature of the solution reached 152° C.) and the reaction solution poured onto a teflon sheet. On cooling to room temperature, the reaction mixture crystalized completely to form translucent tan crystals.

EXAMPLE VII

The reaction solution of Example I was heated to boiling and slowly boiled to effect removal of water until the temperature rose above 110° C. The reaction solution was placed in a refrigerator until crystals formed in the syrupy liquid. The crystals were washed with dilute hydrochloric acid, and on analysis the crystals were found to be ferrous 2-glycine hydrochloride tetrahydrate.

It will be understood that the solid ferrous 2-glycine which has been further stabilized by having up to six additional molecules of glycine bound thereto by coordinate bonds can be recovered or crystalized from an aqueous reaction solution by means other than boiling to remove water. If desired, vacuum drying or flash drying can be used, and the resulting product can be ground to form a white powder which is very soluble in water and stable in dry air but hygroscopic in moist air.

Since glycine and serine are interchangeable metabolites, it is possible to substitute serine for glycine in the foregoing examples to provide an improved source of iron for nutritional and therapeutic use in mammals.

As some mammals are deficient in chloride ion which is essential in the body and serves several important functions, the hydrochloride reaction product of the present invention is preferred for oral administration to mammals.

Other ferrous iron salts, such as ferrous acetate, ferrous citrate, ferrous ascorbate, and ferrous tartrate, can also be used as the non-toxic ferrous salt for reacting with glycine to form the ferrous 2-glycine compound and ferrous 8-glycine. For this reason, the invention is not limited to the reaction products formed by reacting glycine with ferrous chloride or ferrous sulfate used in the specific examples.

EXAMPLE VIII

A liquid containing supplemental iron was prepared by dissolving in water 6.3 grams of ferrous 2-glycine hydrochloride tetrahydrate (to provide 1000 mgs. iron per gallon water) and 8.5 grams, glycine (to provide a six mole excess) in each gallon of water and adjusting the pH of the solution to about pH 4.5 by the addition of citric acid. The solution was provided as drinking water for suckling pigs.

EXAMPLE IX

A liquid feed mix containing supplemental iron was prepared by dissolving in a conventional milk solids solution normally fed to suckling pigs ferrous 8-glycine hydrochloride tetrahydrate to provide 1000 mgs. iron per gallon of milk solid solution. The liquid feed mix was fed to suckling pigs in a conventional manner.

EXAMPLE X

A solid feed mix containing supplemental iron was prepared by admixing ferrous 8-glycine hydrochloride tetrahydrate with a conventional solid feed mix for pigs in an amount sufficient to provide 200 parts per million ferrous iron on a weight basis. The solid feed mixture was fed to pigs in a conventional manner.

Since piglets are usually anemic at birth and rapidly grow extremely anemic during the first 21 days after birth due to the combination of their very rapid growth (4 times birth weight in 3 weeks) and their failure to obtain any significant amount of iron from their sows milk, piglets present a particularly good subject for determining the physiological and nutritional usefulness of iron supplements. Thus, the effectiveness of the reaction product of the present invention, was determined by treating piglets with (1) a standard iron dextran injection which heretofore has been the best means for treating anemia in piglets, (2) ferric ammonium citrate added to the piglets drinking water since this iron salt is the most commonly used additive to the drinking water of piglets, and (3) ferrous 2-glycine solution containing excess glycine.

The following Table I gives the results of comparative tests in which a solution of ferrous 2-glycine hydrochloride reaction product of Example I containing excess glycine was used as the drinking water for two replicates with four piglets per litter and for nine litter at a level of 1000 mgs. iron per gallon of drinking water and wherein the hemoglobin levels indicative of the iron concentration in the blood stream of the piglets were measured.

TABLE I
EFFICACY OF ORAL FERROUS 2-GLYCINE HYDROCHLORIDE COMPLEX[1] IN COMPARISON
TO ORAL FERRIC AMMONIUM CITRATE (FAC) WITH OR WITHOUT IRON DEXTRAN
INJECTION (BABY PIGS)

Tom Evans, Manager
Freeport, Illinois

Veterinarian:
Dr. Mel Wastoupal
Freeport, Illinois

HEMOGLOBIN READINGS (GM/100 ML.)
LITTER NO.

TABLE I-continued

| | I | | | III | | | V | | | VI | | | VIII | | |
|---|---|---|---|---|---|---|---|---|---|---|---|---|---|---|---|
| | No Injection/ No water Treatment | | | FAC/ No Injection | | | FAC/ Plus Iron Injection | | | F 2-G Gl No Iron Inj. | | | F 2-G-Gl Plus Iron Inj. | | |
| | | | | | | | DAY OF AGE | | | | | | | | |
| | 1 | 7 | 14 | 1 | 7 | 14 | 1 | 7 | 14 | 1 | 7 | 14 | 1 | 7 | 14 |
| Pig No. 1 | 11.0 | 9.2 | −1.7 | 11.0 | 9.5 | −1.5 | 10.0 | 9.7 | −0.3 | 9.5 | 10.2 | +0.7 | 10.5 | 12.2 | +1.7 |
| 2 | 10.5 | 8.5 | −2.0 | 12.0 | 10.2 | −1.7 | 9.00 | 10.2 | +1.2 | 10.5 | 12.0 | +1.5 | 8.5 | 10.7 | +2.2 |
| 3 | 8.7 | 7.5 | −1.2 | 10.5 | 8.2 | −2.2 | 11.00 | 10.0 | −1.0 | 10.2 | 12.2 | +2.0 | 12.0 | 13.5 | +1.5 |
| 4 | 9.0 | 9.2 | +0.2 | 12.0 | 7.5 | −2.5 | Died | | | 9.0 | 10.0 | +1.0 | 11.0 | 12.5 | +1.5 |
| 5 | 11.2 | 10.0 | −1.2 | | | | | | | 8.0 | 11.0 | +2.5 | | | |
| 6 | 10.0 | 8.0 | −2.0 | | | | | | | | | | | | |
| 7 | 9.5 | 7.5 | −2.0 | | | | | | | | | | | | |
| Average | | | −1.4 | | | −2.5 | | | 0.00 | | | +1.55 | | | +1.75 |
| Ave.Change | | | −14.2% | | | −17.6% | | | 0.00 | | | +9.55% | | | +16.5% |

| | | | | | | | LITTER NO. | | | | | | | | |
|---|---|---|---|---|---|---|---|---|---|---|---|---|---|---|---|
| | II | | | IV | | | | VII | | | | IX | | | |
| | | | | | | | DAY OF AGE | | | | | | | | |
| | 1 | 7 | 14 | 1 | 7 | 14 | | 1 | 7 | 14 | | 1 | 7 | 14 | |
| Pig No. 1 | 10.0 | 9.2 | +0.7 | 9.0 | 8.0 | −1.0 | | 8.5 | 9.5 | +1.0 | | 10.50 | 11.75 | +1.2 | |
| 2 | 10.5 | 8.0 | −11.5 | 12.0 | 8.5 | −3.5 | | 10.00 | 10.5 | +0.5 | | 8.50 | 10.50 | +2.0 | |
| 3 | 11.0 | 7.7 | −3.2 | 11.0 | 8.5 | −2.5 | | 10.25 | 11.0 | +0.7 | | 12.00 | 12.00 | +0.0 | |
| 4 | 12.0 | 7.0 | −3.0 | 10.5 | 7.5 | −3.0 | | 9.50 | 10.2 | +0.7 | | 11.50 | 12.25 | +0.2 | |
| 5 | 11.5 | 8.2 | −3.5 | | | | | 9.00 | 9.7 | +0.7 | | | | | |
| Average | | | −2.70 | | | −1.7 | | | | +0.94 | | | | +1.00 | |
| Ave.Change | | | −25.0% | | | −16.5% | | | | +9.55% | | | | +9.42% | |

NOTE: To appreciate the total value of the F 2-G treatments, F 2-G gains must be added to losses accorded other treatments.
[1]Contains excess glycine.

A similar series of tests were run using two replicates of tests with 4 pigs per litter and with 10 litters in which gallon of drinking water, and the results are as shown in the following Table II:

TABLE II

EFFICACY OF FERROUS 2-GLYCINE HYDROSULFATE COMPLEX[1] IN COMPARISON TO ORAL FERRIC AMMONIUM CITRATE (FAC) WITH OR WITHOUT IRON DEXTRAN INJECTIONS AND IRON DEXTRAN INJECTION WITHOUT F 2-G OR FAC ON INCREASING HEMOGLOBIN LEFELS OF BABY PIGS*

Reggie Brown Farm.
Macomb, Illinois

Dr. C. R. Hills,
Veterinarian

HEMOGLOBIN READINGS (GM/100 ML.)
2 replicates of tests, 4 pigs per litter tested, 10 litters

| | I | | | III | | | V | | | VII | | | IX | | |
|---|---|---|---|---|---|---|---|---|---|---|---|---|---|---|---|
| | Iron Injection Plain Water | | | No Injection FAC | | | Iron Injection Plus FAC | | | No Injection F 2-GS | | | Iron Injection Plus F 2-GS | | |
| | | | | | | | DAY OF AGE | | | | | | | | |
| | 1 | 7 | 14 | 1 | 7 | 14 | 1 | 7 | 14 | 1 | 7 | 14 | 1 | 7 | 14 |
| Pig No. 1 | 8.5 | 9.0 | 7.7 | 10.6 | 8.5 | 10.5 | 7.2 | 9.8 | 10.5 | 8.5 | 10.5 | died | 8.0 | 10.7 | 11.8 |
| 2 | 10.5 | 8.2 | 7.2 | 8.6 | 8.4 | 11.5 | 10.0 | 10.7 | 11.3 | 7.8 | 12.0 | 14.0 | 8.1 | 9.8 | 12.5 |
| 3 | 8.8 | 8.5 | 5.5 | 9.0 | 9.2 | 10.7 | 9.5 | 10.0 | 11.5 | 6.0 | 9.0 | 12.6 | 8.0 | 9.5 | 12.0 |
| 4 | 9.5 | 9.0 | 6.5 | 8.2 | 9.8 | 10.0 | 9.4 | 10.2 | 10.6 | 6.0 | 9.3 | 12.0 | 7.0 | 12.0 | 12.0 |
| Average (1-4) | 9.3 | 8.7 | 6.9 | 9.1 | 9.0 | 10.7 | 9.0 | 10.2 | 11.0 | 7.1 | 10.2 | 12.9 | 7.7 | 10.5 | 12.1 |
| % of Normal** | 93% | 79% | 57% | 91% | 81% | 89% | 90% | 92% | 91% | 71%+ | 92% | 107% | 78%+ | 95% | 100% |

| | | | | | | | LITTER NO. | | | | | | | | |
|---|---|---|---|---|---|---|---|---|---|---|---|---|---|---|---|
| | II | | | IV | | | VI | | | VIII | | | X | | |
| Pig No. 5 | 8.4 | 11.5 | 11.8 | 9.8 | 8.2 | 9.5 | 9.0 | 13.0 | 11.0 | 10.4 | 12.5 | 13.2 | 7.5 | 12.5 | 14.0 |
| 6 | 9.0 | 11.2 | 9.3* | 9.0 | 10.8 | 9.8 | 8.5 | 10.5 | 9.5 | 9.0 | 9.6 | 13.5 | 7.0 | 11.2 | killed |
| 7 | 10.0 | 12.3 | 10.9* | 12.4 | 8.5 | 9.0 | 8.5 | 10.0 | 12.0 | 10.5 | 11.0 | 12.6 | 7.3 | 10.0 | 13.0 |
| 8 | 9.6 | 11.0 | 10.5 | 10.5 | 9.0 | 9.5 | 8.6 | 12.2 | 11.5 | 10.2 | 12.0 | 12.5 | 6.5 | 11.0 | 12.5 |
| Average (5-8) | 9.2 | 11.5 | 10.6 | 10.4 | 9.1 | 9.5 | 8.6 | 11.4 | 11.0 | 10.0 | 11.3 | 13.0 | 7.1 | 11.2 | 13.2 |
| % of Normal** | 92% | 104% | 88% | 104% | 83% | 79% | 90% | 92% | 91% | 100% | 102% | 108% | 71%+ | 101% | 110% |

*1000 mg. iron per gallon drinking water.
**Suggested normal hemoglobin for peak disease resistance:
 1 Day = 10.0 gms. %   7 Days = 11.0 gms. %   14 Days = 12.0 gms. %
+Note that these piglets averaged nearly 20% below piglets on other treatments, yet outperformed the others greatly. The superiority of F 2-G sulfate is obvious in these tests. It should particularly be noted that F 2-GS gave much better results without an iron injection than ferric ammonium citrate did with an iron injection. All F 2-G tests attained or surpassed "normality" within 14 days, while No other treatment provided normal hemoglobin levels at that time.
[1]Contains excess glycine.

ferrous 2-glycine hydrosulfate was administered by adding to the drinking water at a level of 1000 mgs. per The ferrous iron-glycine reaction products of the present invention are also useful for increasing the iron concentration in the blood of humans. Whereas ferrous sulfate, the most frequently used treatment for increasing the iron concentration in the blood of humans, is absorbed only to the extent of about 10% of the orally administered dose, and ferrous 8-glycine is significantly more completely absorbed when orally administered. Thus, a substantially smaller dose ferrous 8-glycine can be administered to humans and thereby avoiding many of the untoward reactions normally encountered as a result of administering large quantities of iron salts. For example, a dosage level of 100 mgs. per day of ferrous 8-glycine will provide all of the normal or nutritional needs for iron.

I claim:

1. A method of raising the iron concentration of the blood of a mammal, comprising orally administering to a mammal in an amount effective for raising the iron concentration of the blood an orally administrable composition having as the essential source of iron a reaction product comprised essentially of one molar equivalent of an ingestible salt of ferrous iron and glycine in an amount in excess of two molar equivalents of glycine and up to about 8 molar equivalents of glycine for each mole of ferrous iron, said ferrous iron in said reaction product being in a non-ionic form with two moles of glycine ionically bonded to each mole of ferrous iron, said glycine in excess of two moles being covalently bonded to said ferrous iron, and said composition being stable in the pH range of the mammal's gastrointestinal tract.

2. A method as claim 1, wherein said reaction product is a complex of one mole of said ferrous iron salt and in excess of two molar equivalents of glycine and up to 8 moles equivalents of glycine for each mole of ferrous iron, and said glycine in said reaction product being present in an amount which increases the resistance of an aqueous solution of said reaction product to forming a precipitate of iron when a water soluble carbonate ion is admixed therewith.

3. A method as in claim 1, wherein said composition is a solution of said reaction product in an ingestible aqueous liquid having a pH between pH 1 and pH 4.5.

4. A method as in claim 3, wherein said reaction product is the dihydrochloride of ferrous 8-glycine tetrahydrate.

5. A method as in claim 3, wherein said solution has the pH thereof adjusted to between about pH 1 and pH 4.5 by the addition of citric acid.

6. A method as in claim 1, wherein said composition is a mixture of said reaction product and a feed material ingestible by said mammal.

7. An orally administrable iron composition having as the essential source of iron a reaction product comprised essentially of an ingestible salt of ferrous iron and glycine in an amount in excess of two molar equivalents of glycine and up to about 8 molar equivalents of glycine for each mole of ferrous iron which is effective for raising the iron concentration in the blood of a mammal when administered orally, said ferrous iron in said reaction product being in a non-ionic form with two moles of glycine ionically bonded to each mole of ferrous iron, said glycine in excess of two moles being covalently bonded to said ferrous iron, and said composition being stable in the pH range of the mammals gastrointestinal tract.

8. An orally administrable iron composition as in claim 7, wherein said reaction product is a complex of one mole of said iron salt and glycine in excess of two molar equivalents of glycine and up to about 8 moles equivalent of glycine for each mold of said iron salt, and said reaction product characterized by an aqueous solution thereof having increased resistance to forming a precipitate of iron when a water soluble carbonate ion is admixed therewith.

9. An orally administrable iron composition as in claim 7, wherein said composition is a solution of said reaction product in an ingestible aqueous liquid having a pH between pH 1 and pH 4.5.

10. An orally administrable iron composition as in claim 9, wherein said reaction product is the dihydrochloride of ferrous 8-glycine tetrahydrate.

11. An orally administrable iron composition as in claim 9, wherein said solution has the pH thereof adjusted to between about pH 1 and pH 4.5 by the addition of citric acid.

12. An orally administrable composition as in claim 7, wherein said composition is a mixture of said reaction product and a feed material ingestible by said mammal.

* * * * *

UNITED STATES PATENT AND TRADEMARK OFFICE
CERTIFICATE OF CORRECTION

PATENT NO. : 4,183,947
DATED : January 15, 1980
INVENTOR(S) : Vernon L. Cockerill It is certified that error appears in the above-identified patent and that said Letters Patent are hereby corrected as shown below:

Col. 2, line 4, after "mammals" cancel "," and substitute --.--
Col. 3, lines 30-44; the structural formulae should appear as follows:

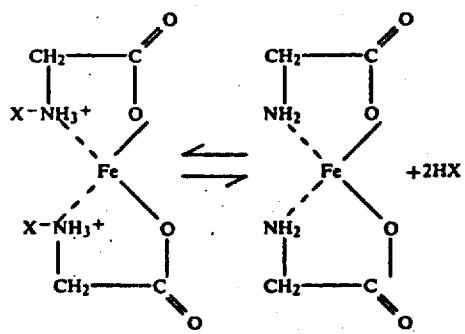

Col. 3, lines 48-60; the structural formulae should appear as follows:

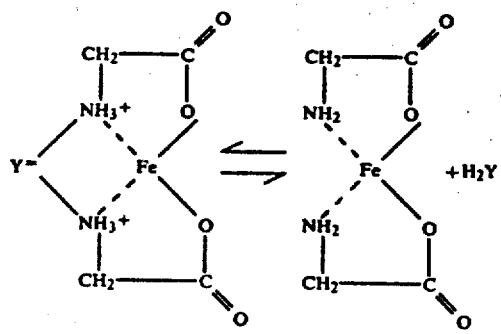

UNITED STATES PATENT AND TRADEMARK OFFICE
CERTIFICATE OF CORRECTION

PATENT NO. : 4,183,947

DATED : January 15, 1980

INVENTOR(S) : Vernon L. Cockerill

It is certified that error appears in the above-identified patent and that said Letters Patent are hereby corrected as shown below:

Col. 4, line 43, cancel "irons" and substitute --ions--.

Col. 8, line 46, cancel "cirtrate" and substitute --citrate--.

Col. 10, In Table II, 3rd line of heading, cancel "LEFELS" and substitute --LEVELS--.

Col. 11, line 6, after "dose" add --of--.

Signed and Sealed this

Third Day of June 1980

[SEAL]

Attest:

SIDNEY A. DIAMOND

Attesting Officer

Commissioner of Patents and Trademarks